United States Patent
Takase

(10) Patent No.: US 6,602,187 B2
(45) Date of Patent: Aug. 5, 2003

(54) ENDOSCOPE HAVING FEATURE IN FLEXIBLE TUBE SECTION CONSTITUTING INSERTION SECTION

(75) Inventor: Seisuke Takase, Hachioji (JP)

(73) Assignee: Olympus Optical Co., Ltd., Tokyo (JP)

( * ) Notice: Subject to any disclaimer, the term of this patent is extended or adjusted under 35 U.S.C. 154(b) by 43 days.

(21) Appl. No.: 09/947,685

(22) Filed: Sep. 6, 2001

(65) Prior Publication Data

US 2002/0032369 A1 Mar. 14, 2002

(30) Foreign Application Priority Data

Sep. 8, 2000 (JP) ........................................ 2000-273793

(51) Int. Cl.$^7$ ................................................ A61B 1/00
(52) U.S. Cl. ........................................ 600/140; 600/133
(58) Field of Search ................................. 600/140, 139, 600/133, 121

(56) References Cited

U.S. PATENT DOCUMENTS 4,899,787 A * 2/1990 Ouchi et al. ................. 138/131
5,058,567 A * 10/1991 Takahashi et al. ........... 600/139
5,217,002 A * 6/1993 Katsurada et al. .......... 600/139
5,394,864 A * 3/1995 Kobayashi et al. ......... 600/146
5,465,710 A * 11/1995 Miyagi et al. ............... 600/139
5,885,207 A * 3/1999 Iwasaka ....................... 600/139
6,083,152 A * 7/2000 Strong ......................... 600/139

FOREIGN PATENT DOCUMENTS

JP  2-283346  11/1990

* cited by examiner

Primary Examiner—Linda C. M. Dvorak
Assistant Examiner—Jocelyn Ram
(74) Attorney, Agent, or Firm—Scully, Scott, Murphy & Presser

(57) ABSTRACT

In an endoscope of the present invention having a feature in a flexible tube section constituting an insertion section, the flexible tube section includes a spiral tube formed by spirally winding a metal strip, a mesh-like tube covering the outside periphery of the spiral tube; and an outer sheath layer composed of resin for covering the outside of the mesh-like tube, wherein when the outer sheath layer is softened by being subjected to a thermal load caused in a high temperature/high pressure steam sterilization process, the outside diameter of the flexible tube section is the same as or smaller than the outside diameter thereof before it is subjected to the thermal load.

4 Claims, 3 Drawing Sheets

ENDOSCOPE HAVING FEATURE IN FLEXIBLE TUBE SECTION CONSTITUTING INSERTION SECTION

This application claims benefit of Japanese Application No. 2000-273793 filed in Japan on Sep. 8, 2000, the contents of which are incorporated by this reference.

BACKGROUND OF THE INVENTION

1. Field of the Invention

The present invention relates to an endoscope that is sterilized with high pressure steam after it is used.

2. Description of the Related Art

Hitherto, there are widely used medical endoscopes capable of observing internal organs and the like in a body cavity by inserting a slender insertion section into the body cavity and executing various types of treatment and remedy using a therapeutic device inserted into a therapeutic device channel when necessary.

Endoscopes used in a medical field observe internal organs and the like by inserting an insertion section into a body cavity and execute various types of treatment and remedy using a therapeutic device inserted into the therapeutic device channel of the endoscopes.

When an endoscope and a therapeutic device which were used once are to be used on another patient, they must be washed and sterilized after the completion of checkup and treatment executed by means of them to prevent infection among patients through the endoscope and the therapeutic device.

Recently, autoclave sterilization (high pressure steam sterilization) is mainly used to disinfect and sterilize medical equipment because the autoclave sterilization permits the medical equipment to be used just after sterilization and its running cost is less expensive.

For example, when the endoscope disclosed in Japanese Patent Unexamined Publication No. 2-283346 is repeatedly subjected to thermal load in high temperature/high pressure steam sterilization, a resin member used as the outer sheath layer of an insertion section composed of a flexible tube section is softened. When a spiral tube disposed inside of the resin member is assembled to the insertion section in a diameter-reduced state, the spiral tube applies a force to the flexible tube section in a diameter increasing direction, whereby the outside diameter of the flexible tube section may be varied in the diameter increasing direction.

Further, when the resin member absorbs moisture and expands, the outside diameter of the insertion section may be varied thereby in the diameter increasing direction.

When the diameter of the insertion section is varied in the diameter increasing direction, a disadvantage arises in that the inserting property of the insertion section is deteriorated as compared with its initial state.

OBJECTS AND SUMMARY OF THE INVENTION

An object of the present invention is to provide an endoscope of which outside diameter of the insertion section is prevented from being increased by a thermal load caused in a high temperature/high pressure steam sterilization process and which is excellent in an insertion property.

Briefly, in an endoscope of the present invention having a feature in a flexible tube section constituting an insertion section, the flexible tube section includes a spiral tube formed by spirally winding a metal strip, a mesh-like tube covering the outside periphery of the spiral tube; and an outer sheath layer composed of resin for covering the outside of the mesh-like tube, wherein when the outer sheath layer is softened by being subjected to a thermal load caused in a high temperature/high pressure steam sterilization process, the outside diameter of the flexible tube section is the same as or smaller than the outside diameter thereof before it is subjected to the thermal load. With this arrangement, even if the insertion section is repeatedly subjected to thermal load caused in a high temperature/high pressure steam sterilization process, the excellent insertion property of the insertion section can be secured at all times without increasing the outside diameter thereof.

DETAILED DESCRIPTION OF THE PREFERRED EMBODIMENTS

An embodiment of the present invention will be described below with reference to the drawings.

The embodiment of the present invention will be described with reference to FIGS. 1 to 3.

Figure 1:
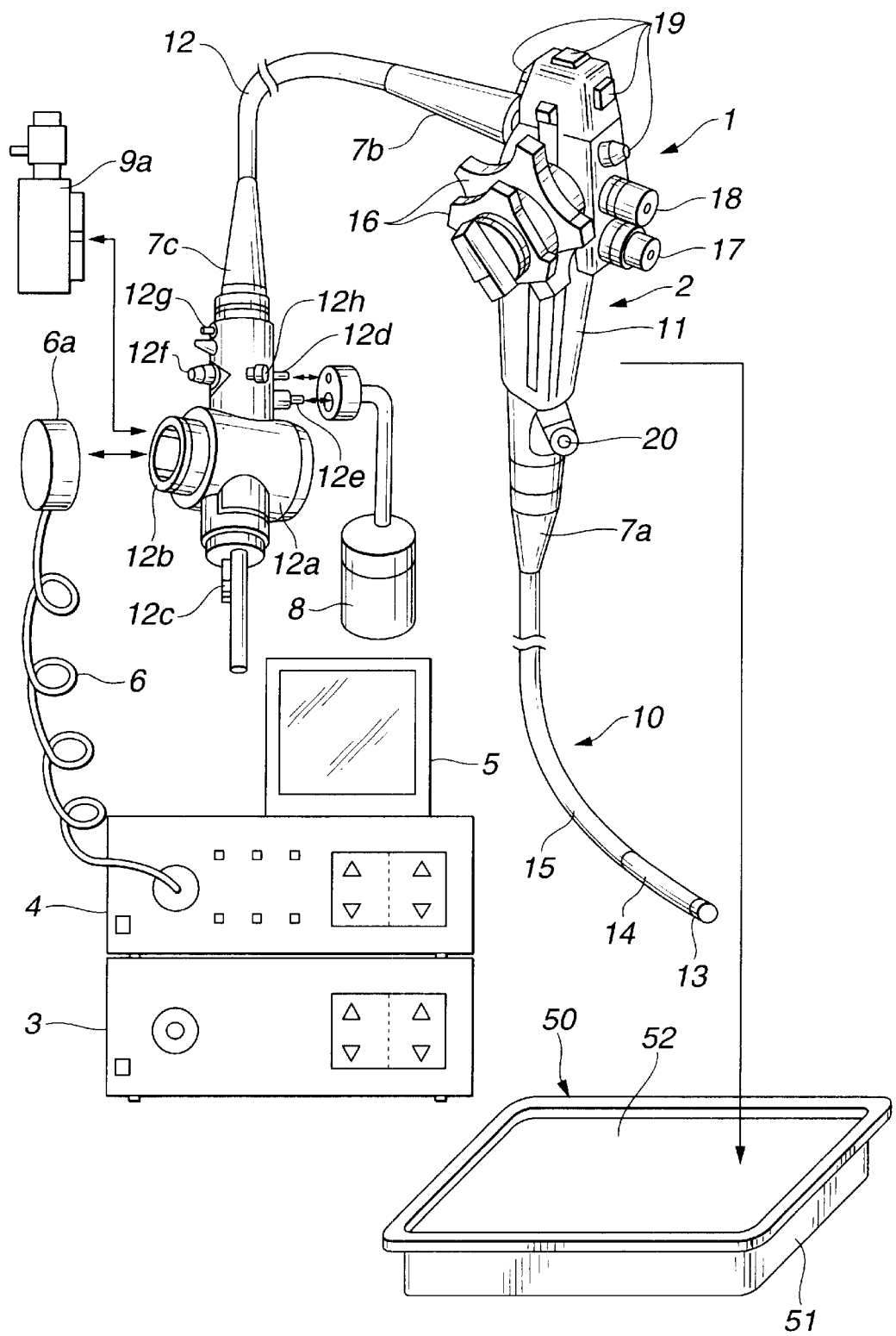
FIG. 1 is a view explaining the arrangement of an endoscope device.

As shown in FIG. 1, an endoscope device 1 of this embodiment is mainly composed of an electronic endoscope (hereinafter, abbreviated as "endoscope") 2, a light source unit 3, a video processor 4, and a monitor 5.

The endoscope 2 includes an image pick up unit. The light source unit 3 supplies illumination light to the endoscope 2. The video processor 4 controls the image pick up unit and converts an image signal obtained by the image pick up unit to, for example, a video signal. The video processor 4 is connected to the monitor 5. Note that reference numeral 50 denotes a sterilization accommodation case to be described later that acts as an endoscope accommodation unit for accommodating the endoscope 2 to be subjected to high temperature steam sterilization.

The endoscope 2 includes an insertion section 10, a manipulation unit 11, and a universal cord 12. The insertion section 10 is slender and flexible. The manipulation unit 11 is connected to the base end of the insertion section 10. The universal cord 12 is flexible and extends from a side of the manipulation unit 11.

A connector 12a that is detachably connected to the light source unit 3 is disposed at an end of the universal cord 12. Connection of the connector 12a to the light source unit 3 permits the illumination light from a lamp (not shown) mounted on the light source unit 3 to be transmitted to a light guide (not shown) in the endoscope 2 so that the illumination light illuminates a portion to be observed.

A manipulation unit bending prevention member 7a composed of an elastic member is disposed at the portion where the insertion section 10 is connected to the manipulation unit 11 to prevent the insertion section and the manipulation unit 11 from being bent sharply. A manipulation unit bending prevention member 7b, which is arranged similarly to the bending prevention member 7a also is disposed at the portion where the manipulation unit 11 is connected to the universal cord 12. Further, a connector bending prevention member 7c arranged in the same manner also is disposed at the portion where the universal cord 12 is connected to the connector 12a.

The slender and flexible insertion section 10 of the endoscope 2 is arranged by sequentially connecting an extreme end hard portion 13, a curving portion 14, and a flexible tube section 15 acting as a soft portion from the extreme end thereof.

The extreme end hard portion 13 is composed of a hard member. An observation window, an illumination window, a gas/water supply nozzle for ejecting washing liquid and gas to the observation window, a suction port for sucking the liquid and dirt, and the like (which are not shown) are disposed at, for example, the extreme end surface of the extreme end hard portion 13.

The bending portion 14 is composed of a plurality of bending elements connected to each other so as to be free to bend.

The flexible tube section 15 has soft, elastic and sophisticated characteristics.

The manipulation unit 11 includes a bending manipulation knob 16 disposed thereto. Suitable manipulation of the bending manipulation knob 16 causes the bending portion 14 to be bent in a desired direction. That is, the extreme end surface, where the observation window and the like are disposed, of the extreme end hard portion 13 can be directed to a desired direction by bending the bending portion 14.

Note that a gas/water manipulation button 17, a suction manipulation button 18, a plurality of remote switches 19 . . . 19, and a therapeutic device insertion port 20 are disposed at the manipulation unit 11 in addition to the above bending manipulation knob 16.

Suitable manipulation of the gas/water manipulation button 17 causes washing liquid and gas to be ejected from the gas/water supply nozzle. Further, manipulation of the suction manipulation button 18 permits body fluid and the like to be sucked through the suction port. The plurality of remote switches 19 . . . 19 control, for example, the video processor 4 remotely. The therapeutic device insertion port 20 communicates with a therapeutic device channel tube to be described later which is disposed in the insertion section of the endoscope 2.

An electric connector unit 12b is disposed at a side of the connector 12a. The signal connector 6a of a signal cord connected to the video processor 4 is detachably connected to the electric connector unit 12b. Connecting the signal connector 6a to the video processor 4 causes the image pick up unit of the endoscope 2 to be controlled as well as causes an image observed through the endoscope to be displayed on the screen of the monitor 5 by creating a video signal by using an image signal transmitted from the image pick up unit.

A ventilation port (not shown) is disposed at the electric connector unit 12b to maintain communication between the inside and the outside of the endoscope 2. Thus, a pressure-regulation-valve-mounted water proofing cap (hereinafter, abbreviated as "water proofing cap") 9a having a pressure regulation valve for closing the ventilation hole is detachably mounted on the electric connector unit 12b of the endoscope 2.

A gas supply mouth ring 12c, a water supply tank pressurizing mouth ring 12d, a liquid supply mouth ring 12e, a suction mouth ring 12f, a pouring mouth ring 12g, and a ground terminal mouth ring 12h are disposed at the connector 12a.

The gas supply mouth ring 12c is detachably connected to a gas supply source (not shown) contained in the light source unit 3. The water supply tank pressurizing mouth ring 12d and the liquid supply mouth ring 12e are detachably connected to a water supply tank 8 acting as a liquid supply source. The suction mouth ring 12f is connected to a suction source (not shown) for executing suction from the suction port. The pouring mouth ring 12g is connected to a water supply unit (not shown) for supplying water. An electric cable is connected to the ground terminal mouth ring 12h. With this arrangement, a high frequency leakage current generated when high frequency treatment and the like are executed can be fed back to a high frequency treatment device (not shown).

The endoscope 2 can be washed after it is used to observation and treatment and arranged so as to be subjected to high pressure steam sterilization. When the endoscope 2 is subjected to the high pressure steam sterilization, the water proofing cap 9a is mounted on the electric connector unit 12b. Further, when the endoscope 2 is subjected to the high pressure steam sterilization, the endoscope 2 is accommodated in the sterilization accommodation case 50.

The sterilization accommodation case 50 is composed of a tray 51 acting as a box member and a lid member 52 for closing the opening of the tray 51. A regulation member (not shown), which is formed in a shape corresponding to that of the endoscope 2, is disposed in the tray 51 to permit the respective units of the endoscope 2 such as the insertion section 10, the manipulation unit 11, the universal cord 12, the connector 12a, and the like to be accommodated at predetermined positions. Further, a plurality of ventilation holes are formed to each of the tray 51 and the lid member 52 to introduce high pressure steam into the sterilization accommodation case 50.

Figure 2:
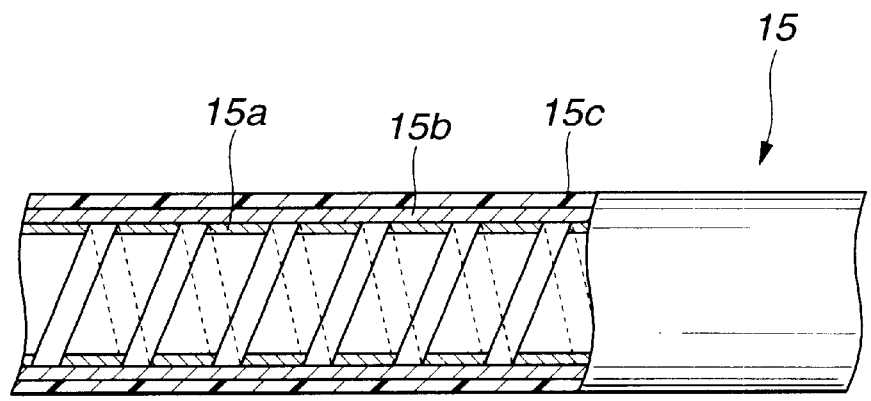
FIG. 2 is a view explaining the arrangement of a flexible tube section.

As shown in FIG. 2, the flexible tube section 15 is composed of a spiral tube 15a, a mesh-like tube 15b, and an outer sheath layer 15c in which order they laminate therearound from the innermost layer thereof. The spiral tube 15a is formed by winding a thin metal strip spirally. The mesh-like tube 15b is formed by knitting metal strands or non-metal strands. The outer sheath layer 15c is composed of, for example, thermoplastic ester type elastomer as a resin material.

Note that the outer sheath layer 15c may be formed of materials such as thermoplastic amide type elastomer, styrene type resin, fluorine type rubber, silicon rubber, and materials obtained by blending them, in addition to the thermoplastic ester type elastomer.

Further, these resin materials used in the outer sheath layer 15c are selected in consideration of durability and an insertion property when they are used and further in consideration of chemical resistance to chemicals and the like which are used in washing and sterilization. Accordingly, some of the resin materials have a thermal deformation temperature which is lower than the temperature condition of a high temperature/high pressure steam sterilization process. Further, some of the resin materials are molded in a drawn state depending upon, for example, an extrusion molding condition when they are molded and deformed when they are released from the stress applied thereto when they are drawn.

Figure 3:
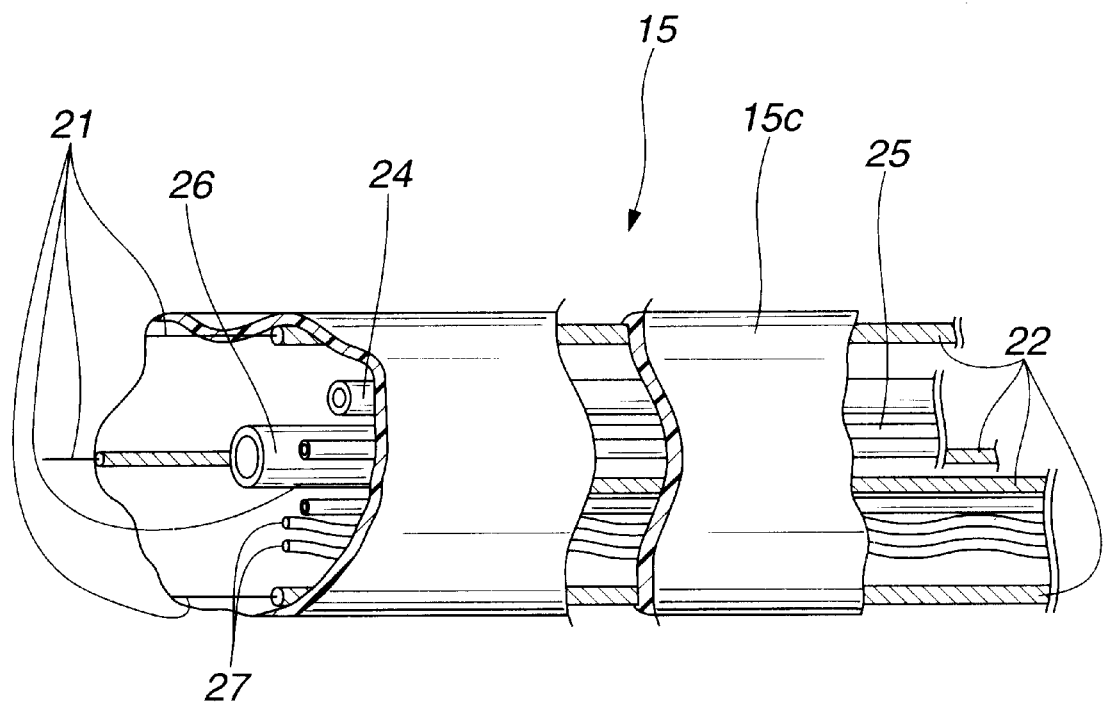
FIG. 3 is a view explaining the arrangement of contained members inserted into the flexible tube section.

As shown in FIG. 3, various built-in members are inserted into the flexible tube section 15. These built-in members are bent metal wires 21, wire-covered metal coils 22, a light guide 24, a gas/water supply tube 25, a therapeutic device insertion channel tube 26, signal cables 27, and the like.

The bent metal wires 21 are moved forward and backward by remotely manipulating the bending manipulation knob 16 so as to bend the bending portion 14. The wire-covered metal coils 22 cover the bent metal wires 21 in a loosely fitted state. The light guide 24 supplies illumination light. The gas/water supply tube 25 and the therapeutic device insertion channel tube 26 are composed of resin tube members.

The respective ends of the gas/water supply tube 25 and the therapeutic device insertion channel tube 26 are locked and fixed to the connecting portion (not shown) of the manipulation unit 11 and to the connecting portion (not shown) of the extreme end hard portion 13, respectively. These connecting portions are coupled with both the ends of the insertion section 10.

The therapeutic device insertion channel tube 26 and the gas/water supply tube 25 are composed of a material having high chemical resistance such as PTFE or the like.

Figure 4:
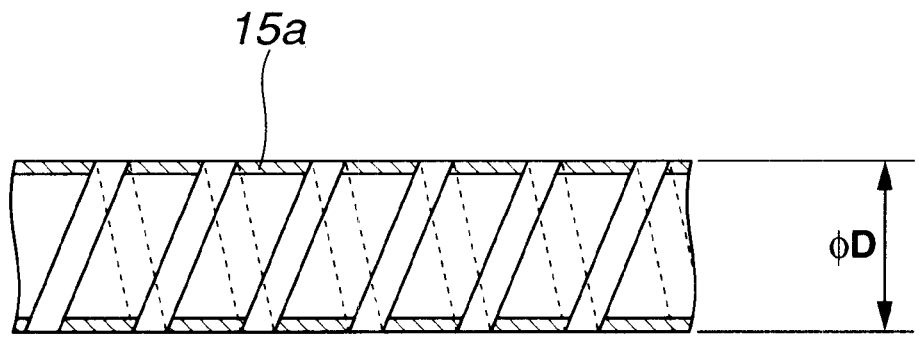
FIG. 4 is a view explaining a state of a spiral tube.

As shown in FIG. 4, when the spiral tube 15a that constitutes the flexible tube section 15 is in a diameter-increased state in which the diameter thereof is increased as compared with a diameter $\Phi D$ which is in a natural state, the spiral tube attempts to return to the natural state (attempts to return to its original diameter). Thus, a force in a shrink direction is applied to the spiral tube 15a. In contrast, when the spiral tube 15a is in a diameter-reduced state in which the diameter thereof is smaller than $\Phi D$ which is in the natural state, a force for increasing the diameter thereof is applied to the spiral tube 15a because it attempts to return to the natural state (attempts to return to its original diameter).

Accordingly, when the spiral tube 15a is assembled to the flexible tube section 15 in the diameter-reduced state at a time the flexible tube section 15 is formed, if the outer sheath layer 15c, which is subjected to a thermal load caused in a high temperature/high pressure steam sterilization process, is thermally deformed at a low temperature, the outer sheath layer 15c is softened as well as the diameter of the spiral tube 15a is varied in a diameter increasing direction. That is, when the flexible tube section 15 is subjected to the thermal load in the high temperature/high pressure steam sterilization process, the diameter thereof is increased as compared with that before it is subjected to the thermal load.

To cope with this problem, in this embodiment, when the flexible tube section 15 is formed, the diameter of the spiral tube 15a is previously increased in a minute amount. That is, the spiral tube 15a is assembled to the flexible tube section 15 in a state that a force is applied to the spiral tube 15a at all times to cause it to attempt to return to the natural state (in a diameter reducing direction).

Typical conditions under which the endoscope 2 is subjected to high pressure steam sterilization will be described here.

As the conditions, there is ANSI/AAMI ST37-1992 which is approved by American National Standards Institute and issued by Association for the Advancement of Medical Instrumentation. According to the Standard, the conditions are such that a sterilizing time is set to 4 minutes at 132° C. in a prevacuum type sterilization process and to 10 minutes at 132° C. in a gravity type sterilization process, respectively.

The temperature condition in a high pressure steam sterilization process is different according to a type of high pressure steam sterilization apparatus and a time set to a sterilization process. Ordinarily, the temperature is set in the range of about 115° C. to 138° C. However, a temperature of about 142° C. can be set in certain types of sterilization apparatus.

In contrast, the time in the high pressure steam sterilization process is different according to the temperature condition in the sterilization process. That is, the time is ordinarily set in the range of about 3 minutes to 60 minutes. Then, a time of about 100 minutes can be set in certain types of sterilization apparatus.

The pressure in a sterilization chamber is set to +0.2 Mpa with respect to the atmospheric pressure in the sterilization process.

Next, an ordinary prevacuum type high temperature/high pressure steam sterilization process for endoscope will be briefly described.

First, the water proofing cap 9a is mounted on the electric connector unit 12b of the endoscope 2 acting as equipment to be sterilized, and the endoscope 2 is accommodated in the sterilization accommodation case 50 and placed in a sterilization apparatus. Since the water proofing cap 9a is mounted on the electric connector unit 12b, the pressure regulation valve is closed and the ventilation port is closed thereby. That is, the inside of the endoscope 2 is hermetically sealed from the outside thereof in a watertight manner. Then, the inside of the sterilization apparatus is set to a pressure reduced state before the high temperature/high pressure steam sterilization process is executed (prevacuum process).

Note that the prevacuum process is a process for penetrating steam to the minute portions of the equipment to be sterilized in the sterilization process. In this prevacuum process, high pressure/high temperature steam is uniformly distributed to the entire equipment to be sterilized by reducing the pressure in the sterilization chamber. In the prevacuum process, the pressure in the sterilization chamber is ordinarily set to about −0.07 to −0.09 Mpa with respect to the atmospheric pressure.

When the pressure in the sterilization chamber is reduced in the prevacuum process, a pressure difference is made such that the external pressure of the endoscope 2 is lower than the internal pressure thereof. Thus, the pressure regulation valve of the water proofing cap 9a is opened, and the inside of the endoscope 2 is communicated with the outside thereof through the ventilation port. With this arrangement, it can be prevented that the pressure difference between the inside pressure of the endoscope 2 and the outside pressure thereof increases. That is, the endoscope 2 can be prevented from being broken by the pressure difference.

Next, the sterilization process for executing sterilization by supplying high temperature/high pressure steam into the sterilization chamber will be described.

In this sterilization process, the sterilization chamber is pressurized. Thus, a pressure difference is made such that the external pressure of the endoscope 2 is higher than the internal pressure thereof. As a result, the pressure regulation valve of the water proofing cap 9a is closed. With this operation, it can be prevented that high pressure steam penetrates into the inside of the endoscope 2 through the ventilation port.

However, high pressure steam gradually penetrates into the inside of the endoscope 2 through O-rings (not shown) and the like as a seal means which are formed of fluorine rubber, silicon rubber, or the like and disposed at the portions where the outer sheath layer 15c, which is formed of polymer, of the flexible tube section 15, and the outside package of the endoscope 2 are connected.

At this time, the pressure, which is obtained by adding the pressure reduced in the prevacuum process and the pressure increased in the sterilization process, is caused to the endoscope 2 from the outside to the inside thereof.

Next, after the completion of the sterilization process, the sterilization chamber is evacuated again and a dry process is executed to dry the equipment having been sterilized.

In this dry process, drying of the endoscope 2 in the sterilization chamber is accelerated by exhausting steam from the sterilization chamber by evacuating the chamber.

In the dry process, the pressure in the sterilization chamber is ordinarily set to about −0.07 to −0.09 Mpa with respect to the atmospheric pressure. Note that the dry process is optionally executed when necessary.

In a pressure reduction process executed after the sterilization process, the pressure in the sterilization chamber is reduced and a pressure difference, in which the external pressure of the endoscope 2 is lower than the internal pressure thereof, is caused. Approximately simultaneously with the occurrence of the pressure difference, the pressure regulation valve of the water proofing cap 9a is opened, and the inside of the endoscope 2 is communicated with the outside thereof through the ventilation port. With this operation, the occurrence of large pressure difference between the inside of the endoscope 2 and the outside thereof can be prevented.

Then, when the internal pressure of the endoscope 2 is approximately equal to the external pressure thereof, the pressure regulation valve of the water proofing cap 9a is closed. Then, the pressure reduction process is finished and the internal pressure of the apparatus is made equal to the atmosphere pressure.

Note that when the high pressure steam sterilization process is entirely finished, the amount of pressure reduced in the pressure reduction process is applied to the outer package portion of the endoscope 2 from the outside to the inside thereof. Then, when the water proofing cap 9a is removed from the electric connector unit 12b, the inside of the endoscope 2 is communicated with the outside thereof through the ventilation hole. With this operation, the pressure in the interior of the endoscope 2 is made equal to the atmospheric pressure and the load applied to the outer package portion of the endoscope 2 by the pressure difference is removed.

With this arrangement, even if the endoscope 2 is repeatedly sterilized in the high temperature/high pressure steam sterilization process as described above and the insertion tube 10 is subjected to a thermal load and the outer sheath layer 15c thereof is softened, an increase in the outside diameter of the flexible tube section 15 can be reliably prevented because the force is applied to the spiral tube 15a in the direction where the diameter thereof is reduced at all times.

Note that while the spiral tube 15a shown in the figure is arranged as a single helical tube, it may be arranged as a double helical tube or a triple helical tube.

Further, a material having a low water absorbing property, that is, a material which is unlike to swell or a material which is shrunk and deformed by the heat applied thereto is selected as the material of the outer sheath layer. However, even if the wall thickness of the outer sheath layer tends to increase when it swells, the outside diameter of the flexible tube section 15 is not increased because the spiral tube 15a, the diameter of which is previously increased, is assembled to the flexible tube section 15 as described above.

Since the spiral tube diameter which is previously increased as compared with that in the natural state thereof is assembled to the flexible tube section in the formation thereof, even if the spiral tube section constituting the inserting section is subjected to thermal load in the high temperature/high pressure steam sterilization process which is executed repeatedly, the outside diameter of the insertion section is not increased and the excellent inserting property thereof can be secured at all times.

Figure 5:
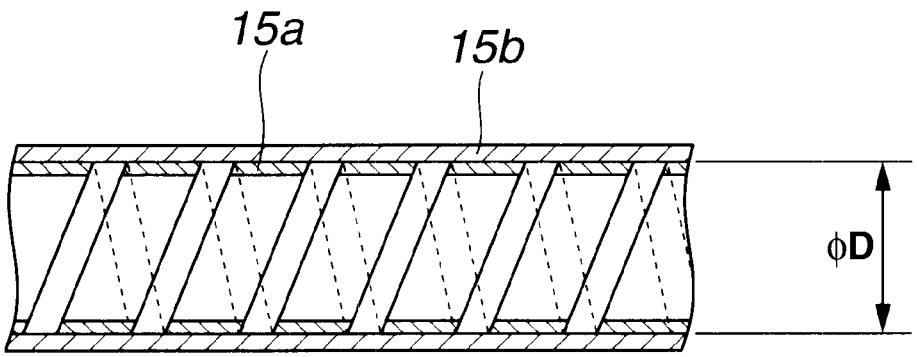
FIG. 5 is a view explaining the relationship between the spiral tube and a mesh-like tube.

Note that when the spiral tube 15a is covered with the mesh-like tube 15b, the mesh-like tube 15b covers the spiral tube 15a, which is in the natural state ($\Phi D$), in intimate contact therewith as shown in FIG. 5. With this arrangement, when the outer sheath layer 15c is softened by being subjected to the thermal load caused in the high temperature/high pressure steam sterilization process and the force can be applied to the spiral tube 15a in the direction where the diameter thereof is increased, an increase in the outside diameter of the flexible tube section 15 can be prevented by the mesh-like tube 15b that is in intimate contact with the spiral tube 15a.

It goes without saying that various different embodiments can be made based on the present invention within the wide range which does not depart from the spirit and scope of the invention.

Further, the present invention is by no means restricted by a particular one of the embodiments except that it is restricted by the accompanying claims.

What is claimed is:

1. An endoscope having a feature in a flexible tube section constituting an insertion section, wherein said flexible tube section comprising: a spiral tube formed by spirally winding a metal strip; a mesh tube covering an outer periphery of said spiral tube; and an outer sheath layer comprising resin for covering an outside of said mesh tube, wherein when said outer sheath layer is softened by being subjected to a thermal load in a high temperature/high pressure steam sterilization process, an outside diameter of said flexible tube section is the same as or smaller than the outside diameter before the thermal load is applied, wherein the spiral tube is n a state where a force is applied in a diameter reducing direction at all times.

2. An endoscope according to claim 1, wherein when said flexible tube section is formed, the spiral tube is in a state such that a diameter is set larger than the diameter thereof when the spiral tube is in a natural state.

3. An endoscope according to claim 1, wherein the temperature set in the high temperature/high pressure steam sterilization process is within the temperature range of about 115° C. to about 140° C.

4. An endoscope according to claim 1, wherein said flexible tube section is formed in a state that said spiral tube is tightened by said mesh tube, whereby the outside diameter of said flexible tube section at an ordinary temperature after being subjected to the thermal load caused in the high temperature/high pressure steam sterilization process is the same as or smaller than the outside diameter thereof before being subjected the thermal load.

* * * * *